United States Patent [19]

Bily

[11] Patent Number: 4,713,341

[45] Date of Patent: * Dec. 15, 1987

[54] STARTER CULTURES OF IMPROVED ACTIVITY FOR DAIRY PRODUCTS AND PROCESS OF MAKING SAME

[76] Inventor: Robert R. Bily, Box 3637, San Jose, Calif. 95156

[*] Notice: The portion of the term of this patent subsequent to Oct. 1, 2002 has been disclaimed.

[21] Appl. No.: 765,694

[22] Filed: Aug. 15, 1985

Related U.S. Application Data

[60] Division of Ser. No. 532,673, Sep. 16, 1983, Pat. No. 4,544,636, which is a continuation-in-part of Ser. No. 507,928, Jun. 27, 1983, abandoned.

[51] Int. Cl.$^4$ .................. C12N 1/20; C12N 1/38; A23C 9/13
[52] U.S. Cl. ................... 435/253; 435/244; 426/34; 426/40; 426/43; 426/61
[58] Field of Search .............. 435/253, 139, 243, 244, 435/260; 426/34, 36, 40, 41, 42, 43, 61, 63, 582, 662

[56] References Cited

U.S. PATENT DOCUMENTS

| | | | |
|---|---|---|---|
| 3,278,313 | 10/1966 | Rhodes | 426/34 |
| 4,110,476 | 8/1978 | Rhodes | 426/41 |
| 4,277,503 | 7/1981 | Bily | 426/40 |
| 4,289,788 | 9/1981 | Cajigas | 426/61 |
| 4,289,789 | 9/1981 | Cajigas | 426/61 |
| 4,343,817 | 8/1982 | Swanson et al. | 426/36 |
| 4,397,878 | 8/1983 | Koide et al. | 426/40 |
| 4,621,058 | 11/1986 | Reddy | 435/253 |
| 4,622,304 | 11/1986 | Reddy | 435/253 |

*Primary Examiner*—Esther M. Kepplinger

[57] ABSTRACT

A process for improving culture activity of acid producing bacteria in dairy media and for providing a buffering effect therein by the addition of lecithin to provide improved starter cultures for dairy products. Various media wherein the activity of acid producing bacteria is enhanced in the presence of lecithin are also described.

2 Claims, No Drawings

STARTER CULTURES OF IMPROVED ACTIVITY FOR DAIRY PRODUCTS AND PROCESS OF MAKING SAME

REFERENCE TO RELATED APPLICATION

This application is a division of application Ser. No. 532,673 filed Sept. 16, 1983, now U.S. Pat. No. 4,544,636 which was a continuation-in-part of application Ser. No. 507,928 filed June 27, 1983 now abandoned.

BACKGROUND OF THE INVENTION

Any improvement in a dairy medium or other media that results in faster acid production, and/or increased activity of an acid producing bacterial culture, is of commercial value to the cultured dairy products industry. Faster acid production, improved culture activity, and increased storage viability are factors which speed up production of cultured products and reduce the amounts of starter culture necessary for bacterial fermentations. Shortened production times and decreased dairy medium requirements will reduce the overall energy consumption in a cultured dairy foods facility because of the large amounts of energy involved in sterilization of media, maintenance of fermentation temperatures, and plant operation and overhead during processing periods.

Improved culture activity and viability during refrigerated storage also allows use of cultures over longer periods of time, necessitating less frequent batch production. Finally, reduced production times and reduced use of starter medium ingredients can represent an economic savings to the cultured dairy food producer.

SUMMARY OF THE INVENTION

The primary object of the present invention is to provide a process which uses the addition of lecithin to dairy media or other media to improve bacterial activity by enhancing growth and/or viability of acid producing bacteria therein, especially lactic acid producing bacteria, and to provide a buffering effect in certain cultured diary media held for long periods of time to increase long term storage viability of said media.

It is another object to provide novel dairy media and other media containing lecithin wherein acid producing bacteria are made more active so that cultured products can be processed more effectively.

It is another object to reduce the amount of energy consumed in dairy operations by increasing production so average energy costs are reduced.

DESCRIPTION OF THE INVENTION

There are a number of steps followed during the production of cultured dairy foods. Conventionally when making cheese, milk is placed in a vat and heated to an appropriate temperature. A starter culture is added to ripen the milk and after an appropriate time, rennet extract, or any of the milk-coagulating catalysts, is mixed in to initiate the coagulation process unless the milk is set with starter culture only. The amount of milk, starter culture and rennet extract or coagulating catalyst is closely controlled as are many other ingredients which are added for various purposes. The resulting mixture is allowed to remain quiet until a curd forms. The curd is then cut and cooked prior to draining or dipping, knitting, salting, pressing and any special applications. The above process is that conventionally followed in the manufacture of most cheeses but other methods can and do apply.

In addition to the use of such starter cultures to ripen milk for cheese production, starter cultures ae used in other acidic, culture dairy products such as buttermilk, sour cream, yogurt and the like.

My prior U.S. Pat. No. 4,277,503 did not deal with the production and improved use of dairy starter cultures but instead taught the use of lecithin to increase the yield of cheese by adding lecithin to milk, ordinarily after the addition of a conventional starter culture, prior to the coagulation of the milk in the cheese making process. The present invention differs from my prior patent in that: (a) an improved method, starter culture products and special media are provided and (b) the improved starter cultures and special media are useful in a wide variety of products and are not confined to cheese production.

Thus, the process of this invention may be used for preparing various dairy media or other special carrier media suitable for the growth or suspension of acid producing bacteria and increasing the activity of the bacteria when added thereto. These media can be any media that are beneficial to or not harmful to acid producing bacteria, i.e. lactic starter cultures. Since other acids are produced in the fermentation of dairy media, this process is not limited to the activity of lactic acid producing bacteria but includes all acid producing bacteria produced in cultured dairy media. Therefore, the use of this invention is to improve the activity and viability of all acid producing bacteria, especially lactic acid producing bacteria in dairy media, or special carrier media that may be used. Some examples of lactic starter cultures are bulk starter cultures, frozen cultures, concentrated bacterial cultures of any type, frozen concentrated bulk starters, and the like. A dairy medium is any medium capable of supporting acid producing bacteria that has as one of its ingredients, or as its only ingredient, a dairy product such as whey, milk, cream or any milk derivative such as whey protein, casein, lactose or other milk components that can be used as acid producing dairy media. Collectively these are referred to as "lactic media." A special carrier medium is a broader term and includes additionally any medium useful as a pre-incubation, resuspending or acid producing medium that is harmless to lactic starter cultures and that can be used to solubilize, mix and carry lecithin in suspension with said cultures prior to inoculation of a lactic medium with said cultures. Therefore, non-limiting examples of carrier media are lactic media as described and liquids such as water that are harmless to acid producing bacteria and that have been mixed with lecithin according to examples shown and that serve as media that allow for the mixture of bacteria cultures with the lecithin dispersed within said media, Other ingredients may be present. For example, in acid producing dairy media such as bulk starter media, ingredients like phosphate salts, dextrose, pancreatin, yeast, etc. may be present in addition to either milk or whey or both combined. When preparing any acid producing dairy media, lecithin is added directly to the milk, whey, cream or other dairy product being used as the media for the enhancement of the activity of acid producing bacteria which are added thereafter, i.e., in the production of bulk starter. Furthermore, when "direct-vat-set" cultures are used as starters such as those that have been concentrated and/or frozen for direct addition to dairy products, or when lecithin is added to bulk starter medium that has already been inoculated, a lecithin premix carrier medium with lecithin mixed therein such as uncultured lactic medium, or other media that can serve as a harmless pre-incubation, resuspending or acid producing carrier medium suitable for saturating starter cultures with lecithin when admixed therein is made as shown below and these "direct-vat-set" cultures or bulk starter cultures not previously produced with lecithin are first added to said premix carrier medium to saturate said bacteria with lecithin before their addition to the dairy food to be fermented. The object is to surround the bacteria with an ample supply of lecithin before addition to the dairy product to be fermented. This action will enhance the activity of the bacteria when they are added to the dairy food about to be fermented in the same way bacterial activity is enhanced in bulk starters which are previously produced with lecithin incorporated in the starter media prior to inoculation as examples will show. The lecithin used can be any lecithin derived from animal or vegetable sources and normally is a natural mixture of phospholipids or phosphatides derived from soybeans. Liquid lecithin can be used, but powdered lecithin that is substantially oil free is easier to mix in aqueous solutions. Lecithin is best added to the chosen medium by prolonged high shear agitation and heat. The presence of these two factors will guarantee total solubility of the lecithin in the medium. The temperature of the medium should be at least 140° F. at the time the lecithin is solubilized by easier mixability. Generally speaking, lecithin is added in amounts ranging from about 0.01 to 10% by weight of the medium.

The method in which the lecithin is added to the media must be carefully controlled. For example, if the lecithin is added to a dairy media before it is inoculated, it is best to add the lecithin directly to said dairy media while employing high shear agitation and high heat as shown, for example, in the production of bulk starter media. If the dairy media has been previously inoculated, it is best not to vigorously agitate said media when adding the lecithin after inoculation due to bacterial shear and oxygen toxicity. In this case, the lecithin should be added to a quantity of a premix carrier medium as shown beforehand and said lecithin should be premixed therein as shown. Once the lecithin and chosen premix carrier medium have been vigorously mixed together under high heat, the mixture can be added to the starter cultures with gentle agitation. It is best to add the lecithin and chosen premix carrier medium to the starter cultures and let this entire mixture stand for approximately 1 to 10 minutes before adding the entire mixture to the dairy food product medium which is to be fermented so that saturation of the bacteria with lecithin can occur.

When mixing the lecithin with the various media described, different methods of mixing under high shear agitation can be used. The lecithin can be mixed vigorously with various dairy media in a regular culture tank before inoculation and processed in the same way as any bulk starter culture media is processed; or if a premix carrier medium is to be made first, the lecithin can be mixed with a premix carrier medium weighing approximately 10 to 30 times more than the lecithin in a large high shear mixer such as a Viking mixer, or the lecithin can be added to the premix carrier medium via a funnel and reciprocating high speed pump that recirculates said carrier medium and lecithin combination vigorously back through the pump until solubility of the lecithin is achieved.

The following non-limiting examples illustrate preferred embodiments of my invention.

EXAMPLE 1

Lowfat milk containing 2% fat and 10% solids-not-fat was autoclaved at 250° F. for 10 minutes and then cooled to a temperature of 120° F. Metarin K powdered soybean lecithin (Lucas Meyer, Inc.) was weighed into a portion of the warmed milk to produce an 18% w/v solution, which was then blended at high speed on a Waring Commercial Blender for 10 minutes. The blended lecithin solution was then diluted by addition of three parts of warmed sterile lowfat milk to obtain a final lecithin concentration of 4.5%. The control medium consisted of sterile lowfat milk without lecithin added. Initial pH of each medium was 6.60.

Six *Streptococcus cremoris* starter culture strains (DPL Culture Service, Inc., San Francisco) that are used in commercial dairy operations were inoculated into the 4.5% lecithin medium and the control milk. Two of the strains were obtained as freeze-dried DPL Bulk Set concentrated starter powders and were inoculated in the proportion recommended for commercial bulk starter preparation. The remaining four strains were inoculated at a 1% level from fresh milk cultures that had been ripened at 73° F. for 18 hours. This level of inoculum simulated handling of factory grown intermediate starter cultures.

Each inoculated starter medium was incubated at 73° F. for a 16 hour period, comparable to commercial bulk starter incubation conditions. The pH of each culture was measured at the end of the 16 hours. The pH of cultures grown by the method of the present invention, i.e., a starter medium employing 4.5% lecithin was found to be consistently higher than the control cultures.

Each ripened 16 hour culture was inoculated at a 5% level into pasteurized nonfat milk containing 9.0% solids-not-fat. Samples were incubated at 88° F. to simulate commercial short-set cottage cheese-making conditions. The time required for production of a curd with cutting firmness was recorded as shown by Table 1. Nonfat milk inoculation with cultures grown in the medium of the invention exhibited superior set times compared to those of control grown cultures for at least five out of six strains studied.

TABLE 1

| Strain | Inoculum | Starter with 4.5% Lecithin | | Control Milk Starter | |
| --- | --- | --- | --- | --- | --- |
| | | 16 h pH | Cheese Set Time* | 16 h pH | Cheese Set Time |
| A | 1% Fresh | 4.62 | 3:30 | 4.50 | 3:40 |
| B | 1% Fresh | 4.53 | 3:30 | 4.46 | 3:40 |
| C | 1% Fresh | 4.65 | 3:30 | 4.54 | 3:45 |
| D | 1% Fresh | 4.53 | ≦3:30 | 4.44 | 3:30 |
| E | Conc. Powder | 4.85 | 4:00 | 4.76 | 4:10 |
| F | Conc. Powder | 4.74 | 3:30 | 4.63 | 3:40 |

*Cheese set time at 88° F. using a 5% inoculum of 16 hour starter (hours:minutes)

EXAMPLE 2

Control and 4.5% lecithin starter media were prepared in the same manner as set forth in Example 1. Three *Streptococcus cremoris* strains were inoculated into each medium at a 1% level, as in Example 1. Each inoculated starter culture was incubated at 73° F. for 17 hours to permit maximum acid development and cell growth. At the end of the incubation period, each ripened culture was checked for pH and for cell density. The medium was Ellikers Agar from Difco.

Table 2 shows that the pH of cultures grown in the medium of the invention was consistently higher than the pH of control cultures. This could be interpreted either as indicative of retarded cell growth, and hence lesser acid production, in the lecithin grown cultures, or it could be indicative of a buffering effect by the lecithin medium. Additional data presented in Table 2 shows that the same density of cells was achieved in both the medium of the invention and in the control medium. This indicates that the higher pH of the lecithin enhanced cultures is not due to retarded cell growth but to a superior buffering effect. Such buffering action in the growth medium of lactic acid bacteria is generally recognized as beneficial to *culture activity and stability*.

TABLE 2

| Strain | Initial cfu/ml* | Starter with 4.5% Lecithin 17 h pH | 17 h cfu/ml* | Control Milk Starter 17 h pH | 17 h cfu/ml* |
| --- | --- | --- | --- | --- | --- |
| A | $1.9 \times 10^7$ | 4.52 | $9.8 \times 10^8$ | 4.41 | $1.0 \times 10^9$ |
| B | $1.3 \times 10^6$ | 4.53 | $3.1 \times 10^8$ | 4.40 | $3.2 \times 10^8$ |
| C | $5.4 \times 10^7$ | 4.63 | $2.5 \times 10^9$ | 4.57 | $2.4 \times 10^9$ |

*cfu/ml = viable colony forming units or cells per ml

EXAMPLE 3

Control and 4.5% lecithin milk media were again prepared as in Example 1. All media were tempered to a temperature of 88° F. prior to inoculation. Two *Streptococcus cremoris* strains that had been ripened in lowfat milk at 73° F. for 18 hours were inoculated at a 2% level into the tempered control and lecithin media. Cultures were incubated at 88° F., the optimum growth temperature for *Streptococcus cremoris*.

The growth of each culture was followed throughout the incubation period by monitoring acid development. Cell densities were checked at time of inoculation, in the middle of the fermentation, and in the ripened culture.

Table 3 shows that, despite the buffering effects of lecithin, the pH of both strains enhanced in the lecithin medium fell more rapidly than in the controls, particularly in the last half of the fermentations. Cell densities were very similar at the 2.5 hour point, but both cultures made with lecithin showed superior cell densities in the ripened culture.

TABLE 3

| | Strain A 4.5% Lecithin | | Strain A Control | | Strain B 4.5% Lecithin | | Strain B Control | |
| --- | --- | --- | --- | --- | --- | --- | --- | --- |
| time | pH | cfu/ml | pH | cfu/ml | pH | cfu/ml | pH | cfu/ml |
| 0 | 6.50 | $1.9 \times 10^7$ | 6.50 | $1.9 \times 10^7$ | 6.50 | $1.3 \times 10^6$ | 6.50 | $1.3 \times 10^6$ |
| 2.5 h | 5.99 | $7.7 \times 10^7$ | 5.95 | $6.7 \times 10^7$ | 6.09 | $1.8 \times 10^7$ | 6.12 | $2.4 \times 10^7$ |
| 3.5 h | 5.55 | — | 5.54 | — | 5.70 | — | 5.71 | — |
| 4. h | 5.27 | — | 5.28 | — | 5.42 | — | 5.53 | — |
| 4.5 h | 4.97 | — | 5.11 | — | 5.15 | — | 5.33 | — |
| 5 h | 4.78 | — | 4.88 | — | 4.92 | — | 5.10 | — |
| 5.5 h | 4.66 | $4.3 \times 10^8$ | 4.68 | $3.5 \times 10^8$ | 4.75 | $6.6 \times 10^8$ | 4.84 | $5.1 \times 10^8$ |

EXAMPLE 4

An experiment similar to Example 3 was performed using a premix carrier medium containing 10% lecithin (Lec. in tables) by weight of the carrier medium premix weighing 200 pounds, employing a wider range of strains, and monitoring growth by pH development only in the food product milk. The premix carrier medium with lecithin was prepaed by adding 20 pounds of Metarin K powdered lecithin to 200 pounds of lowfat milk at 140° F. and blending the warm mixture at high speed for 5 minutes. The 220 pounds of premix medium with the lecithin was tempered to 88° F. and admixed with 5% of freshly ripened milk culture of each culture strain individually. This lecithin-culture-carrier medium premix was allowed to stand for about 5 minutes and added at a 10% level to the food product milk. Six commercial strains of *Streptococcus lactis* and *cremoris*, representing a range of activity, temperature, and bacteriophage sensitivity properties, were each incubated separately in said product milk at 88° F. Similar trains that were not enhanced with lecithin were added to food product milk individually to serve as controls.

Table 4 shows that the rate of culture development, as represented by acid production, was more rapid in the product milk with the lecithin-culture-carrier medium premix added thereto than in the control milk without lecithin enhanced cultures for all six strains studied.

TABLE 4

| Strain | Culture Treatment | pH 3 h | 3.5 h | 4 h | 4.5 h | 5 h | 6 h |
| --- | --- | --- | --- | --- | --- | --- | --- |
| G | Control | 6.08 | 5.95 | 5.79 | 5.61 | 5.48 | 5.15 |
| | Lec. Enhanced | 6.11 | 5.97 | 5.77 | 5.61 | 5.43 | 5.02 |
| H | Control | 5.82 | 5.60 | 5.34 | 5.14 | 4.92 | 4.62 |
| | Lec. Enhanced | 5.77 | 5.46 | 5.14 | 4.93 | 4.72 | 4.54 |
| I | Control | 5.95 | 5.72 | 5.46 | 5.22 | 5.00 | 4.71 |
| | Lec. Enhanced | 5.86 | 5.57 | 5.28 | 5.08 | 4.90 | 4.66 |
| J | Control | 5.93 | 5.68 | 5.47 | 5.26 | 5.11 | 4.75 |
| | Lec. Enhanced | 5.79 | 5.49 | 5.22 | 5.00 | 4.85 | 4.60 |
| K | Control | 5.90 | 5.62 | 5.37 | 5.15 | 4.97 | 4.65 |
| | Lec. Enhanced | 5.75 | 5.44 | 5.16 | 4.90 | 4.74 | 4.57 |
| L | Control | 5.99 | 5.75 | 5.58 | 5.40 | 5.25 | 4.86 |
| | Lec. Enhanced | 5.95 | 5.66 | 5.41 | 5.19 | 5.01 | 4.70 |

EXAMPLE 5

The effect of the lecithin-culture-carrier medium premix on the activity of *Lactobacillus acidophilus*, a thermophilic lactic acid producing bacterium, was tested at two incubation temperatures. Both the lecithin-culture-carrier medium premix and control were prepared as in Example 4. The special lecithin premix was tempered to either 100° or 113° F. and admixed with 5% of a fresh milk culture of *Lactobacillus acidophilus*. The mixture was allowed to stand for 10 minutes and then added to the food product milk which was to be fermented.

Growth of the cultures was monitored by following pH development over a period of 6.5 hours. Table 5 shows that acid development at both 100° and 113° F. was more rapid in the milk using the culture enhanced in the lecithin-carrier medium premix than in the control milk fermented without lecithin enhanced cultures.

TABLE 5

|      | L. acidophilus, 100° F. | | L. acidophilus, 113° F. | |
|------|------------------------|---------|------------------------|---------|
|      | Lec. Enhanced | Control | Lec. Enhanced | Control |
| to   | 6.50 | 6.50 | 6.50 | 6.50 |
| 2 h  | 6.18 | 6.29 | 6.09 | 6.13 |
| 3.5 h| 6.04 | 6.14 | 5.91 | 5.96 |
| 5 h  | 5.87 | 6.01 | 5.72 | 5.82 |
| 6.5 h| 5.77 | 5.83 | 5.66 | 5.75 |

EXAMPLE 6

The effect of 1.0% lecithin milk medium on *Streptococcus cremoris* culture activity after storage at 40° F. was examined. 1% lecithin by weight was added to milk as shown beforehand and compared to control milk without lecithin. Three strains of *Streptococcus cremoris* that had been ripened in lowfat milk at 73° F. for 18 hours were inoculated at a 1% level into 1.0% lecithin and control media that had been tempered to 73° F. Cultures were incubated at 73° F. for 18 hour and chilled to 40° F.

Activity of each culture was tested on days 0 (freshly ripened), 1, 4 and 7 by inoculating at a 5% level into pasteurized nonfat milk containing 9.0% solids-not-fat, incubating at 88° F. and checking the pH after 3.5 hours. Table 6 shows that all three strains grown in 1.0% lecithin medium show a slight to significant improvement in acid-producing activity on Day 4 and a substantial improvement in activity on Day 7 as compared to their activity in control milk medium.

TABLE 6

| Days 40° | Strain C* | | Strain H* | | Strain J* | |
|----------|-----------|---------|-----------|---------|-----------|---------|
|          | 1.0% Lec  | Control | 1.0% Lec  | Control | 1.0% Lec  | Control |
| 0        | 5.06      | 4.99    | 5.05      | 5.00    | 5.08      | 5.03    |
| 1        | 5.25      | 5.18    | 5.24      | 5.20    | 5.21      | 5.21    |
| 4        | 5.22      | 5.23    | 5.31      | 5.36    | 5.20      | 5.32    |
| 7        | 5.45      | 5.60    | 5.86      | 5.98    | 5.56      | 5.72    |

*pH at 5% inoculum after 3.5 hours at 88° F.

EXAMPLE 7

The effect of very low levels of lecithin on culture activity in five strains of *Streptococcus cremoris* and *lactis* was examined. Test milk medium was prepared by adding either 0.05% or 0.10% by weight of Metarin K powdered lecithin to lowfat milk at 140° F., blending the warm mixture at high speed for 5 minutes, and then autoclaving at 250° F. for 10 minutes. Test milk medium with and without lecithin was cooled to 73° F. and inoculated with 1% of freshly ripened milk culture of each of the strains to be tested. Cultures were incubated at 73° F. for 18 hours and then tested for pH and activity.

Activity of each ripened culture was checked by inoculating at a 2% level into 9.0% nonfat milk, incubating at 88° F., and checking the pH after 3.6 hours. Table 7 shows that pH development for all five cultures was generally superior for 0.05% and 0.10% lecithin milk grown cells as compared to the control. Though the exact levels at which lecithin benefits various representative strains may differ, a measurable improvement in culture activity was observed in all strains examined at either 0.05% or 0.10% lecithin.

TABLE 7

|        | Control Medium | | 0.05% Lec. Medium | | 0.10% Lec. Medium | |
|--------|----------------|-----------|-------------------|-----------|-------------------|-----------|
|        | 18 h           |           | 18 h              |           |                   |           |
| Strain | pH             | Activity* | pH                | Activity* | 18 h pH           | Activity* |
| H      | 4.40           | 5.36      | 4.44              | 5.28      | 4.48              | 5.30      |
| I      | 4.39           | 5.23      | 4.41              | 5.16      | 4.44              | 5.18      |
| J      | 4.34           | 5.21      | 4.34              | 5.28      | 4.34              | 5.15      |
| K      | 4.29           | 4.86      | 4.31              | 4.81      | 4.34              | 4.87      |
| L      | 4.34           | 5.15      | 4.36              | 5.10      | 4.38              | 5.09      |

*Final pH at 9.0% nonfat milk after inoculation with 2% of test culture and incubation for 4 hours at 88° F.

EXAMPLE 8

The effect of presoaking bacterial cultures in a solution of water and lecithin on culture activity after addition to product milk is examined using one strain of *Streptococcus cremoris*. In this example, water acted as the special carrier medium to solubilize the lecithin and resuspend and preincubate the bacterial cultures added thereto. This special medium was prepared by adding 1.25% Metarin K powdered lecithin by weight to distilled water at 145° F. and employing high shear agitation for 2 minutes. The mixture was then sterilized at 12 pounds for 10 minutes. As a control, an equal amount of distilled water without lecithin was sterilized at 12 pounds for 10 minutes.

Both of these media were admixed with 20% of fresh mother culture and preincubated for 10 minutes in the first test and 18 hours in the second test. These tests were done at 70° F. Activity of each culture was checked by inoculating at a 2% level into 10% nonfat milk, incubating at 88° F., and checking the pH at 4 hours and 5 hours. A further control was included by adding 2% of fresh mother culture directly into 10% nonfat milk under identical methods but without lecithin or preincubation.

Table 8 shows that pH reduction, i.e. acid development for cultures preincubated in the special carrier media made with lecithin, was superior to the controls made without lecithin. It was also apparent that the lecithin enhanced cultures created firmer sets more quickly in the test milks.

TABLE 8

|                                    | 4 hr. pH | 5 hr. pH |
|------------------------------------|----------|----------|
| Culture Preincubation-18 hours     |          |          |
| 1% Lecithin enhanced (water)       | 5.61     | 5.30     |
| Control (water)                    | 5.72     | 5.41     |
| Culture Preincubation-10 minutes   |          |          |
| 1% Lecithin enhanced (water)       | 5.40     | 4.92     |
| Control (water)                    | 5.43     | 5.01     |
| No Culture Preincubation           |          |          |
| Control (milk)                     | 5.46     | 5.03     |

I claim:

1. A method of making bacterial cultures for use in producing a lactic food product comprising the steps of combining acid-producing bacteria with sterile culture media, further combining at least 0.01% lecithin by weight of the sterile culture media to the acid-producing bacteria and sterile culture media, then incubating the mixture of sterile culture media, acid-producing bacteria and lecithin to produce an active, viable bacteria culture of enhanced activity that may be added to a lactic medium for producing a foot product.

2. The method of claim 1, and further comprising the step of incubating the mixture of acid-producing bacteria and sterile culture media prior to the addition of lecithin.

* * * * *

UNITED STATES PATENT OFFICE
CERTIFICATE OF CORRECTION

Patent No. 4,713,341    Dated December 15, 1987

Inventor(s)   Robert R. Bily

It is certified that error appears in the above-identified patent and that said Letters Patent are hereby corrected as shown below:

```
col. 1, line 43; "diary" should be -- dairy --
col. 4, line 46; "inoculation" should be -- inoculated --
col. 6, line  3; "prepaed" should be -- prepared --
col. 6, line 15; "trains" should be -- strains --
col. 6, line 68; "culture" should be -- cultures --
col. 7, line 61; "3.6" should be -- 3.5 --
col. 8, line 63; "foot" should be -- food --
```

Signed and Sealed this

Seventh Day of June, 1988

*Attest:*

DONALD J. QUIGG

*Attesting Officer*    *Commissioner of Patents and Trademarks*